US005697543A

United States Patent [19]
Burdorff

[11] Patent Number: 5,697,543
[45] Date of Patent: Dec. 16, 1997

[54] LINEAR STAPLER WITH IMPROVED FIRING STROKE

[75] Inventor: Mark A. Burdorff, Loveland, Ohio

[73] Assignee: Ethicon Endo-Surgery, Inc., Cincinnati, Ohio

[21] Appl. No.: 614,216

[22] Filed: Mar. 12, 1996

[51] Int. Cl.⁶ ............................................. A61B 17/068
[52] U.S. Cl. ........................ 227/176.1; 227/19; 227/178.1
[58] Field of Search ........................... 227/19, 175.1, 227/176.1, 178.1

[56] References Cited

U.S. PATENT DOCUMENTS

| | | | |
|---|---|---|---|
| 4,527,724 | 7/1985 | Chow et al. | 227/19 |
| 4,566,620 | 1/1986 | Green et al. | 227/19 |
| 4,573,622 | 3/1986 | Green et al. | 227/19 |
| 4,728,020 | 3/1988 | Green et al. | 227/19 |
| 5,071,052 | 12/1991 | Rodak et al. | 227/178 |
| 5,137,198 | 8/1992 | Nobis et al. | 227/178.1 |
| 5,307,976 | 5/1994 | Olson et al. | 227/178 |
| 5,318,221 | 6/1994 | Green et al. | 227/178 |
| 5,452,836 | 9/1995 | Huitema et al. | 227/176 |
| 5,465,895 | 11/1995 | Knodel et al. | 227/176 |
| 5,579,978 | 12/1996 | Green et al. | 227/19 |

*Primary Examiner*—Scott A. Smith
*Attorney, Agent, or Firm*—Mathew S. Goodwin

[57] ABSTRACT

A linear stapler particularly adapted for open surgical procedures is disclosed. Staples are fired when tissue is clamped between the cartridge and anvil of the staple fastening assembly of the stapler, and the firing trigger is pivotally rotated in a counterclockwise direction from an unfired position to a fired position adjacent the hand grip of the frame of the stapler. Resistance to the pivotal rotation of the firing trigger independent of the staple fastening assembly is provided to inhibit the surgeon from inadvertently firing the staples or partially firing the staples from the cartridge against the anvil. The firing bar is sandwiched between two spacer plates secured to the firing bar, and a stationary slot pin must overcome the resistance of detents displayed on slots in the spacer plates when the firing bar is moved distally to fire the staples. An audible signal is also provided to alert the surgeon when staples have been fully fired. One of the spacer plates has a signal spring and pin which interacts with a signal ramp attached within the frame. As staples are being fired, the ramp deflects the pin, and when firing is complete, the spring disengages from the ramp and impacts the inside of the frame to provide an audible signal. Although the invention is described in connection with an open linear stapler, it is broadly applicable to other surgical fastening instruments, including endoscopic linear staplers.

12 Claims, 9 Drawing Sheets

LINEAR STAPLER WITH IMPROVED FIRING STROKE

BACKGROUND OF THE INVENTION

This invention relates to linear staplers which initially clamp bodily tissue and then fire staples into the clamped tissue for fastening. More specifically, it relates to linear staplers which have a firing trigger to effect the firing of staples contained in a staple cartridge for formation against an anvil to fasten the clamped tissue.

Linear staplers typically include a cartridge containing a plurality of staples displayed in offset vertical rows, and an anvil facing the cartridge for staple formation. The cartridge and anvil are movable relative to each other from an open, spaced-apart position to a closed position where the cartridge and anvil are adjacent each other. In the open position, bodily tissue can be positioned between the cartridge and anvil. In the closed position, the tissue is clamped between the cartridge and anvil, and the clamped tissue is therefore positioned to receive the staples for tissue fastening.

A linear stapler can be particularly designed for applications involving minimally invasive surgery, where surgery is performed through small openings, or conventional "open" surgery. In order to accomplish the steps of clamping the tissue and firing staples into the clamped tissue, linear staplers typically have a frame for gripping the stapler, and clamping and firing triggers or levers mounted to the frame. When tissue is placed between the cartridge and anvil, the surgeon squeezes or depresses the trigger or lever to clamp the tissue. Subsequently, the surgeon squeezes the firing trigger to fire the staples and fasten the tissue.

In some instances, when tissue is clamped between the cartridge and anvil of the linear stapler, the surgeon inadvertently applies pressure to the firing trigger before he is ready to do so. This unfortunately causes a partial firing of the vertical rows of staples from the cartridge. If the stapler is inadvertently partially fired, then the tissue may be improperly fastened, or the surgeon may need to replace the partially spent cartridge and retire the stapler, resulting in an excess of time, waste and expense. Ideally, it would be desirable if the surgeon could apply pressure to the firing trigger without immediately initiating the firing of staples from the cartridge.

Once the clamped tissue is properly fastened following the complete firing of the staples from the cartridge, it is often desirable to provide means to determine if the stapler has indeed been fully fired. Accordingly, it would be useful if, upon squeezing the firing trigger to fire all of the staples from the cartridge, there would be some type of audible indicator to alert the surgeon that the stapler has been fired and the stapling operation has been completed.

Accordingly, it would be beneficial if a linear stapler were developed which offered the surgeon the flexibility to partially squeeze the firing trigger of the stapler without immediately initiating the firing of staples from the cartridge into the tissue. Also, it would be beneficial if such a stapler included a readily discernible indicator to the surgeon that the stapler has been successfully fired. Furthermore, it would be beneficial if these two desirable features could be incorporated into a linear stapler in a simple and cost effective fashion, without the need for numerous additional parts or significant expense.

SUMMARY OF THE INVENTION

The invention is a surgical stapling instrument. In a preferred embodiment of the invention, the instrument has a frame, a staple fastening assembly, first and second elongated structural plates, a clamping and firing transmission assembly, a clamping actuator, a firing trigger and resistance means. Each of the components of this instrument will now be set forth in more detail.

The frame of the instrument is at a first end of the instrument. It is adapted for gripping and manipulating the instrument. It has a body portion, and a hand grip which descends from the body portion of the frame.

The staple fastening assembly of the instrument is at an end opposite that of the frame of the instrument. The staple fastening assembly includes a cartridge which displays a plurality of vertical rows of slots for containing staples. It also includes an anvil which faces the cartridge for forming staples from the cartridge. The cartridge and anvil are movable toward each other from a spaced position for positioning tissue between the cartridge and anvil to a closed position for clamping the positioned tissue.

The first and second elongated structural plates couple the frame of the instrument to the staple fastening assembly. These plates are spaced from each other.

The clamping and firing transmission assembly of the instrument is fitted between the elongated structural plates. This transmission assembly has first and second elongated closure plates. The closure plates are spaced from each other, and the first plate is adjacent the first structural plate and the second plate is adjacent the second structural plate. In addition, an elongated firing bar is fitted between the first and second elongated closure plates.

The clamping actuator is located at the frame. It is operatively connected to the clamping and firing transmission assembly. When the clamping actuator is actuated, the clamping and firing transmission assembly move distally. This distal movement causes the cartridge and anvil to move to their closed position for clamping the tissue.

The firing trigger is pivotally mounted to the body portion of the frame. It pivotally rotates in a counterclockwise direction from an unfired position to a fired position. In the unfired position, the firing trigger is spaced from the hand grip. In the fired position, it is positioned adjacent the hand grip. When the firing trigger is rotated from its unfired position to its fired position, the firing bar of the clamping and firing transmission assembly moves distally. This distal movement causes the firing of staples from the cartridge against the anvil for corresponding staple formation.

Lastly, the resistance means provides resistance to the distal movement of the firing bar when the firing trigger is pivotally rotated from its unfired position to its fired position. The resistance means is in communication with the clamping and firing transmission assembly, but independent of the staple fastening assembly. That is, the means for providing the resistance to the distal movement of the firing bar is independent of the resistance to distal firing movement created when the staples are ejected from the cartridge against the anvil within the staple fastening assembly.

The surgical stapling instrument described in the preferred embodiment of this invention relates generally to a linear stapler adapted particularly for open surgical procedures. Significantly, the means for providing resistance to the distal movement of the firing trigger when the trigger is pivotally rotated gives the surgeon the desired flexibility to apply pressure to the firing trigger without immediately initiating the firing of staples. This is so because to fire the staples, the surgeon must first consciously overcome the increased resistance which the resistance means adds to the firing stroke. If pressure on the firing trigger is only partially or inadvertently applied, the surgeon will not overcome this increased resistance, and the firing bar will not move distally to inadvertently fire staples. Staples will be fired only if sufficient force is applied to the trigger which overcomes the resistance means to pivotally rotate the trigger from its unfired to fired positions. In this way, an important advantage is achieved.

In a more preferred embodiment of the invention, the surgical stapling instrument of this invention further comprises means in communication with the clamping and firing transmission assembly independent of the staple fastening assembly for providing a signal when the firing trigger is rotated to the fired position. Ideally, this signal is an audible signal. Such a signal provides the added advantage of providing the surgeon with a discernible indicator when the stapler has been successfully fired. Additionally, a visual signal is also provided because the firing trigger remains adjacent the clamping trigger when firing is complete.

In a broader embodiment of the invention, the surgical stapling instrument of this invention can be adapted for not only open surgical procedures, but also endoscopic surgical procedures as well. Accordingly, in this broader embodiment, the instrument has a firing transmission assembly which includes an elongated firing bar interposed between the staple fastening assembly and the frame. Similarly, the firing trigger is pivotally mounted to the body portion of the frame for pivotal counterclockwise rotation from an unfired position spaced from the hand grip to a fired position adjacent the hand grip. When the cartridge and anvil are in their closed position for clamping tissue, and the firing trigger is rotated from its unfired to fired positions, the firing bar of the firing transmission assembly moves distally causing firing of the staples from the cartridge against the anvil for staple formation. Once again, the instrument has means in communication with the firing transmission assembly independent of the staple fastening assembly for providing resistance to the distal movement of the firing bar when the firing trigger is pivotally rotated from its unfired to fired positions.

Accordingly, the surgical stapling instrument of this invention can be used in endoscopic and conventional open surgical procedures. The preferred instruments of this invention are linear staplers, particularly linear staplers adapted for open surgical procedures.

DETAILED DESCRIPTION OF THE PREFERRED EMBODIMENTS

Figure 1:
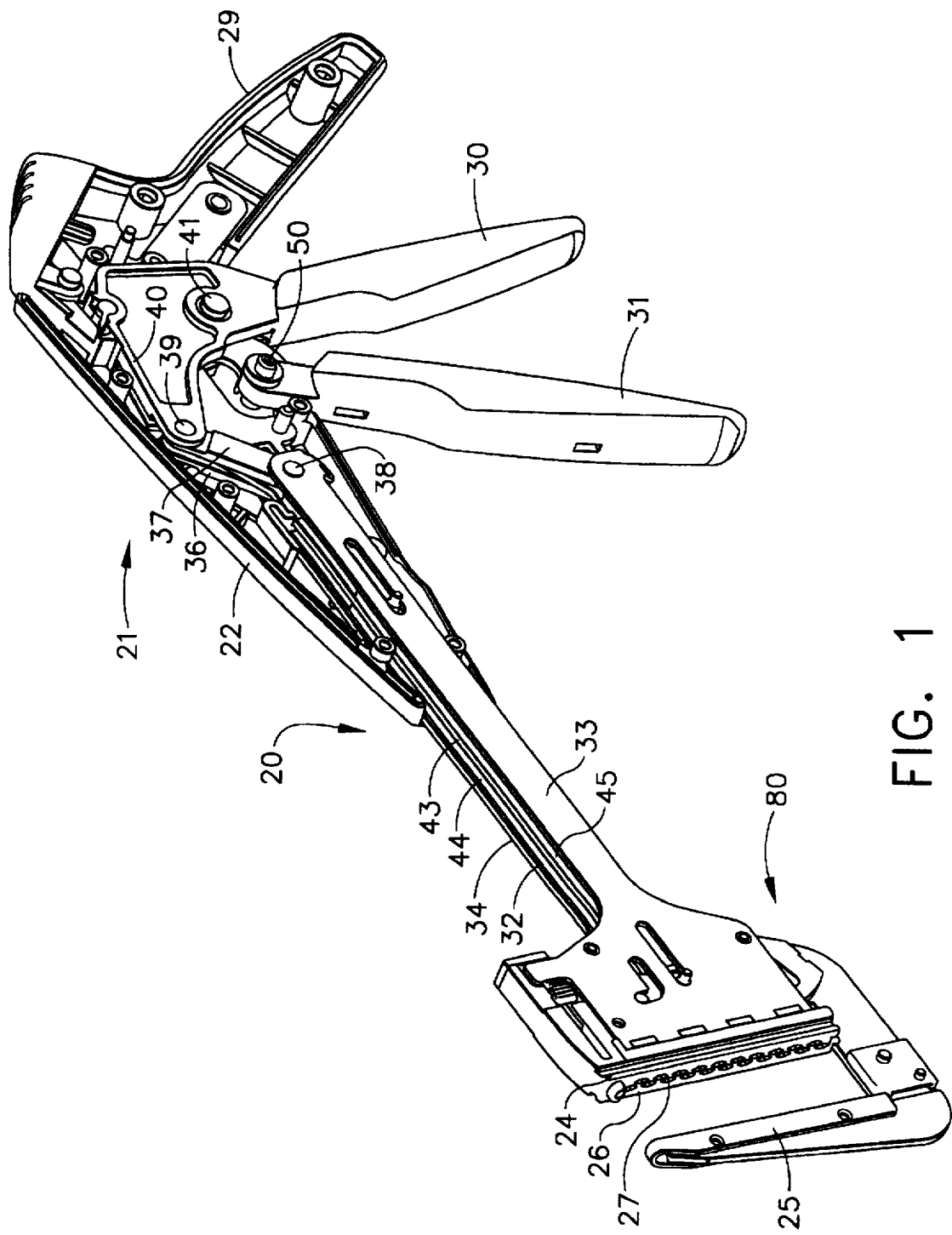
FIG. 1 is an isometric view of a preferred embodiment of this invention in the form of a surgical linear stapler. The left hand shroud and the left hand structural plate (often referred to as the "hook") have been removed from the stapler to expose its internal components. Four operating springs have also been removed for clarity.
Figure 2:
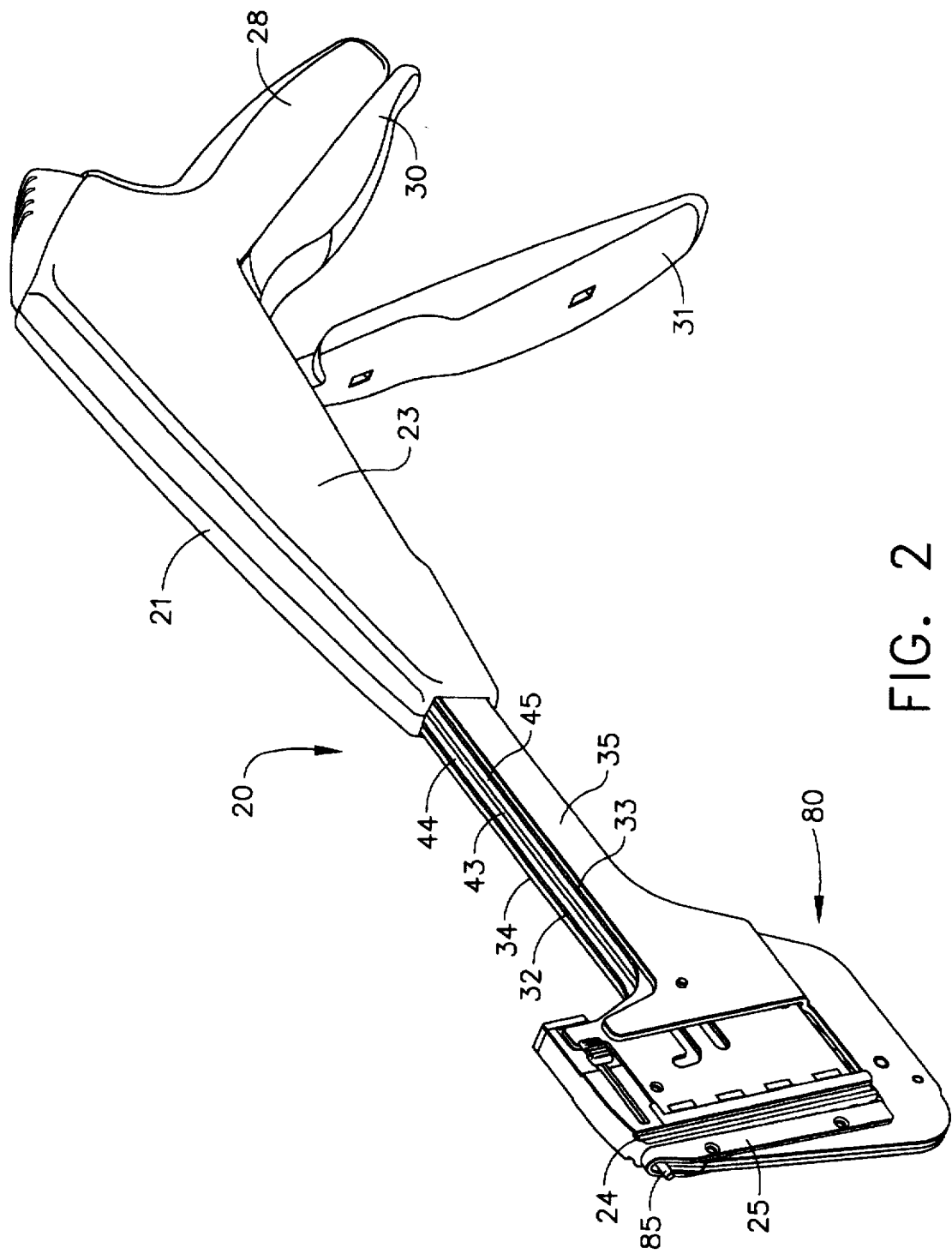
FIG. 2 is an isometric view of the surgical linear stapler of FIG. 1 in which the staple fastening assembly of the stapler is positioned in the closed position to clamp tissue.
Figure 3:
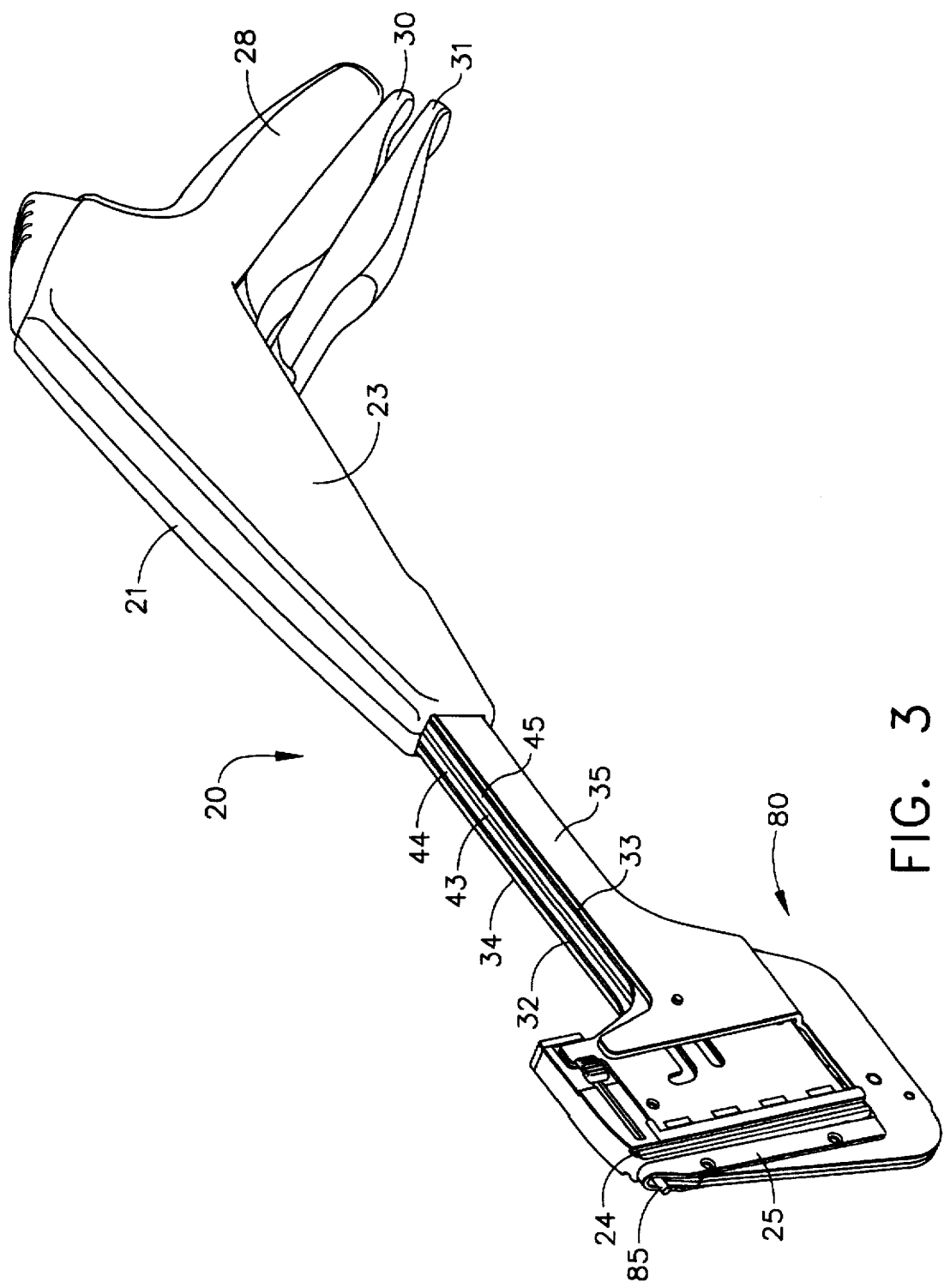
FIG. 3 is an isometric view of the surgical linear stapler of FIG. 1 in which the staple fastening assembly of the stapler is positioned in the fired position. In this position, staples have been fired from the cartridge against the anvil of the surgical fastening assembly of the stapler.

Referring to FIG. 1 in combination with FIGS. 2 and 3, there is shown a linear surgical stapler 20. The stapler has a frame 21 at a first proximal end and an end effector 80 at an opposite distal end. Right and left hand structural plates, or hooks, 34 and 35, respectively, connect the frame to the end effector of the instrument (the left hand hook is not shown in FIG. 1). The frame has a right hand shroud 22 coupled to a left hand shroud (the left hand shroud is not shown in FIG. 1). The frame also has a body portion 23 to grip and maneuver the stapler (see FIGS. 2 and 3). The end effector is a staple fastening assembly which has a cartridge 24 and an anvil 25. The cartridge has a tissue contacting surface 26 which displays a plurality of staple-containing slots 27 in vertical rows. Staples (not shown) are fired from the cartridge against the staple-forming surface of the anvil (not shown) which faces the tissue-contacting surface of the cartridge.

The frame of the stapler includes a hand grip 28 which the surgeon grasps with the palm of his hand (see FIGS. 2 and 3). The hand grip is formed from the coupling of the right hand shroud handle 29 (see FIG. 1) to the left hand shroud handle (the left hand shroud handle is not shown in FIG. 1). Pivotally extending from the underside of the frame are a clamping trigger 30 and a firing trigger 31. The linear surgical stapler illustrated in FIG. 1 is shown with the clamping and firing triggers in their unactuated positions. Consequently, the cartridge is spaced from the anvil for the placement of tissue between the cartridge and anvil.

Referring briefly to FIGS. 2 and 3, them is illustrated what happens when the clamping and firing triggers are sequentially squeezed toward the hand grip to actuate the staple fastening assembly of the linear stapler. When the clamping trigger is squeezed to pivotally rotate it from its open position to its closed position adjacent the forward end of the hand grip as illustrated in FIG. 2, the tissue-contacting surface of the cartridge and the staple-forming surface of the anvil are adjacent to each other. Consequently, if tissue were placed between the cartridge and anvil when the cartridge and anvil were in their spaced position, it would be clamped between the cartridge and anvil when the cartridge and anvil are in their closed position shown in FIG. 2. When the cartridge and anvil move towards each other from their spaced to closed positions in response to pivotal rotation of the clamping trigger, a tissue retaining pin 85 moves forwardly from the cartridge through an opening in the anvil. In this position, tissue which has been placed between the cartridge and anvil can be properly positioned, and retention of the tissue between the cartridge and anvil can be assured. Additionally, during the pivotal rotation of the clamping trigger, the firing trigger has rotated counterclockwise toward the hand grip to enable the surgeon to grasp the firing trigger for the firing of staples. Accordingly, the firing trigger is now in position for the surgeon to squeeze it to staple the tissue. When the firing trigger has been fully squeezed to fire the staples, as shown in FIG. 3, the firing trigger rests in near proximity to the clamping trigger in the embodiment particularly illustrated in the drawings.

Figure 5:
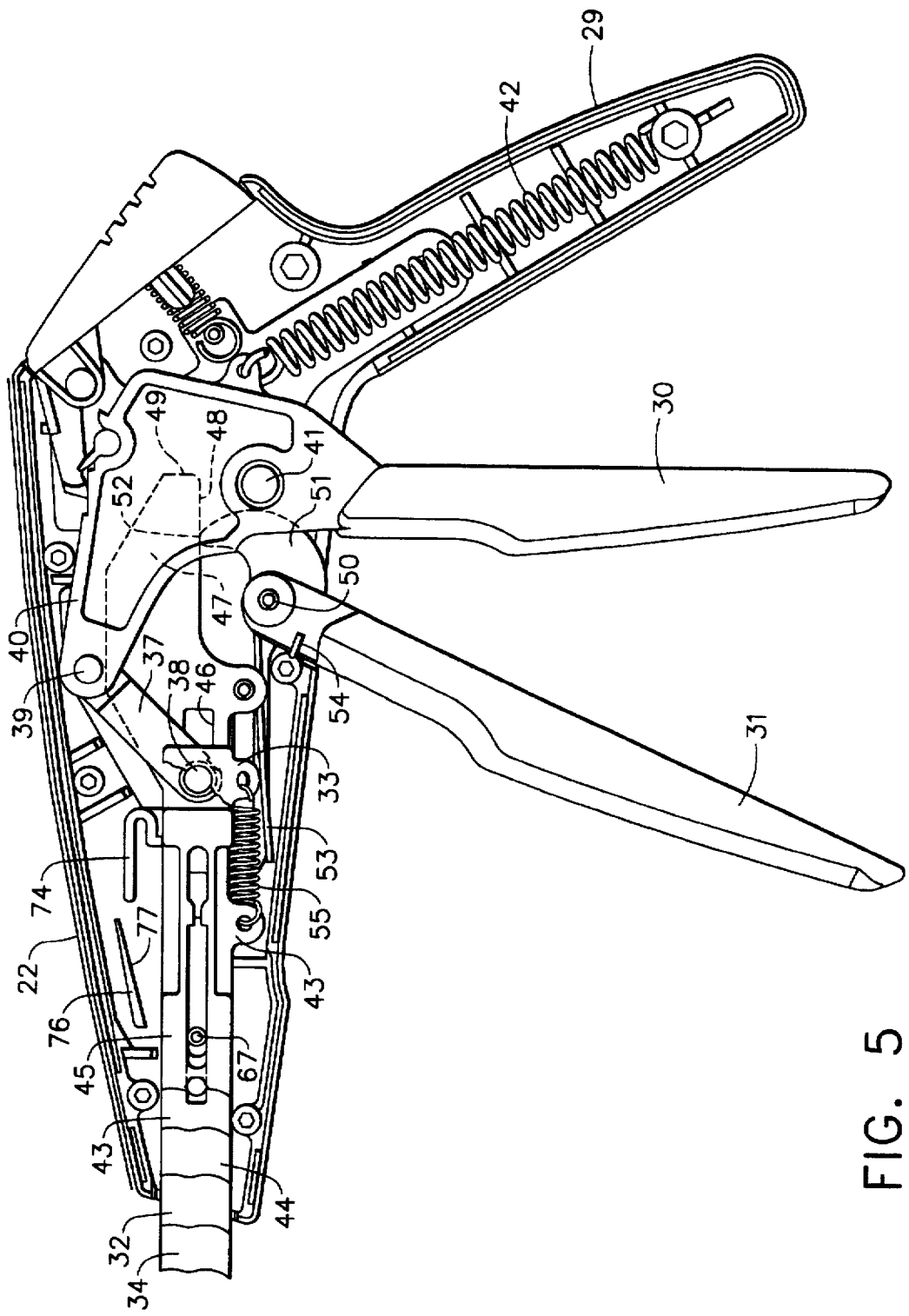
FIG. 5 is a truncated side elevation view of the frame portion of the linear stapler with the left hand shroud and the left hand hook removed to expose internal parts. Only the proximal end of the left hand closure plate is included in order to show the proximal half of the left hand spacer plate. The plates at the left end of the figure are cut off in succession for ease of identification.

Referring once again to FIG. 1 in combination with FIG. 5, a more detailed description of the components of the linear stapler can be provided. The clamping components of the clamping and firing transmission assembly of the stapler includes right and left hand elongated closure plates 32 and 33, respectively, extending from the frame into the surgical fastening assembly. The plates are positioned between the right and left hand hooks, 34 and 35, respectively. Right and left hand clamping links 36 and 37, respectively, are pivotally attached at the proximal ends of the right and left hand closure plates by a first integral clamping link pin 38. At the opposite end of the clamping links, the clamping links are pivotally attached by a integral clamping link pin 39 to the slotted clamping arm link 40. The slotted clamping arm link is pivotally mounted to the frame of the stapler at the clamping trigger pivot pin 41. The clamping trigger descends from the slotted clamping arm link for pivotal rotation about the clamping trigger pivot pin toward and away from the hand grip. A closure spring 42 housed within the hand grip of the frame is secured to the slotted clamping arm link to provide a desired resistance when the surgeon squeezes the clamping trigger toward the hand grip, and to bias the clamping trigger toward the open position.

The firing components of the clamping and firing transmission assembly will now be described. There is an elongated firing bar 43 extending from the frame into the surgical fastening assembly of the linear surgical stapler. The firing bar is positioned between the right and left hand closure plates, 32 and 33, respectively. In order to prevent undesirable deflection of the firing bar during firing, right and left hand spacer plates, 44 and 45, respectively, are positioned adjacent each side of the firing bar between the firing bar and the right and left hand closure plates. The firing bar has a rectangular receiving slot 46 in that portion of the firing bar which is housed within the frame (see FIG. 5). The first integral clamping link pin 38 extends through the receiving slot. The firing bar also has a proximal end section 47. The underside of the proximal end section of the firing bar has a sliding surface 48. The proximal end section also has a terminal side engagement surface 49 extending from the sliding surface. The firing trigger is pivotally mounted to the frame by a firing trigger pivot pin 50 spaced from the clamping trigger pivot pin 41 so that each of the pivot pins pivots about mutually independent axes. The firing trigger includes an arcuate firing trigger link 51 extending from the firing trigger at the firing trigger pivot pin to an apex 52 which rests on the sliding surface of the proximal end section of the firing bar. Within the frame, the firing trigger is attached to first and second firing spring arms, 53 and 54, respectively. The firing spring arms support a torsion spring on the right half of the firing trigger (not shown). Finally, a firing bar return spring 55 is secured to the underside of the firing bar at that portion of the firing bar within the frame to bias the firing bar toward its unfired position.

Figure 6:
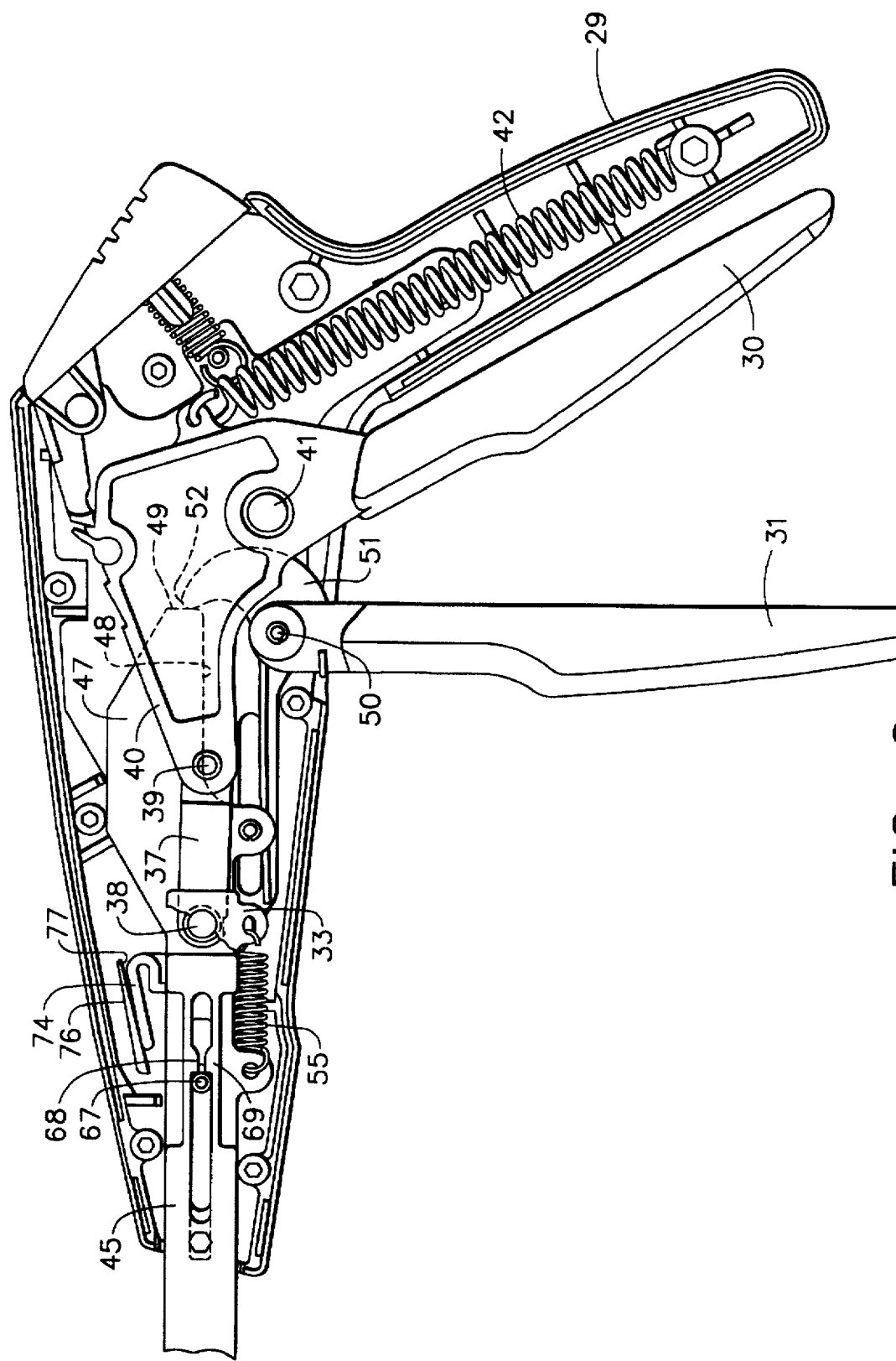
FIG. 6 is a truncated side elevation view as in FIG. 5 showing the clamping trigger of the linear surgical stapler in the closed position as shown in FIG. 2.

Referring now to FIG. 6, when the clamping trigger is squeezed toward the hand grip, the slotted clamping arm link 40 and the clamping links 36 and 37 move distally within the receiving slot 46 of the firing bar. This distal movement causes the closure plates 32 and 33 to correspondingly move distally. Likewise, the firing bar 43 concurrently moves distally with the closure plates because the first integral clamping link pin 38, to which the clamping links are attached, extends through the receiving slot in the firing bar. When the clamping trigger is positioned in its closed position as shown in FIG. 3, the apex 52 of the arcuate firing trigger link 51 moves from the sliding surface 48 of the proximal end section of the firing bar to the terminal side engagement surface 49. Consequently, the firing trigger is now positioned for pivotal rotation toward the clamping trigger to cause continued distal movement of the firing bar for staple firing once the surgeon squeezes the firing trigger.

Figure 4:
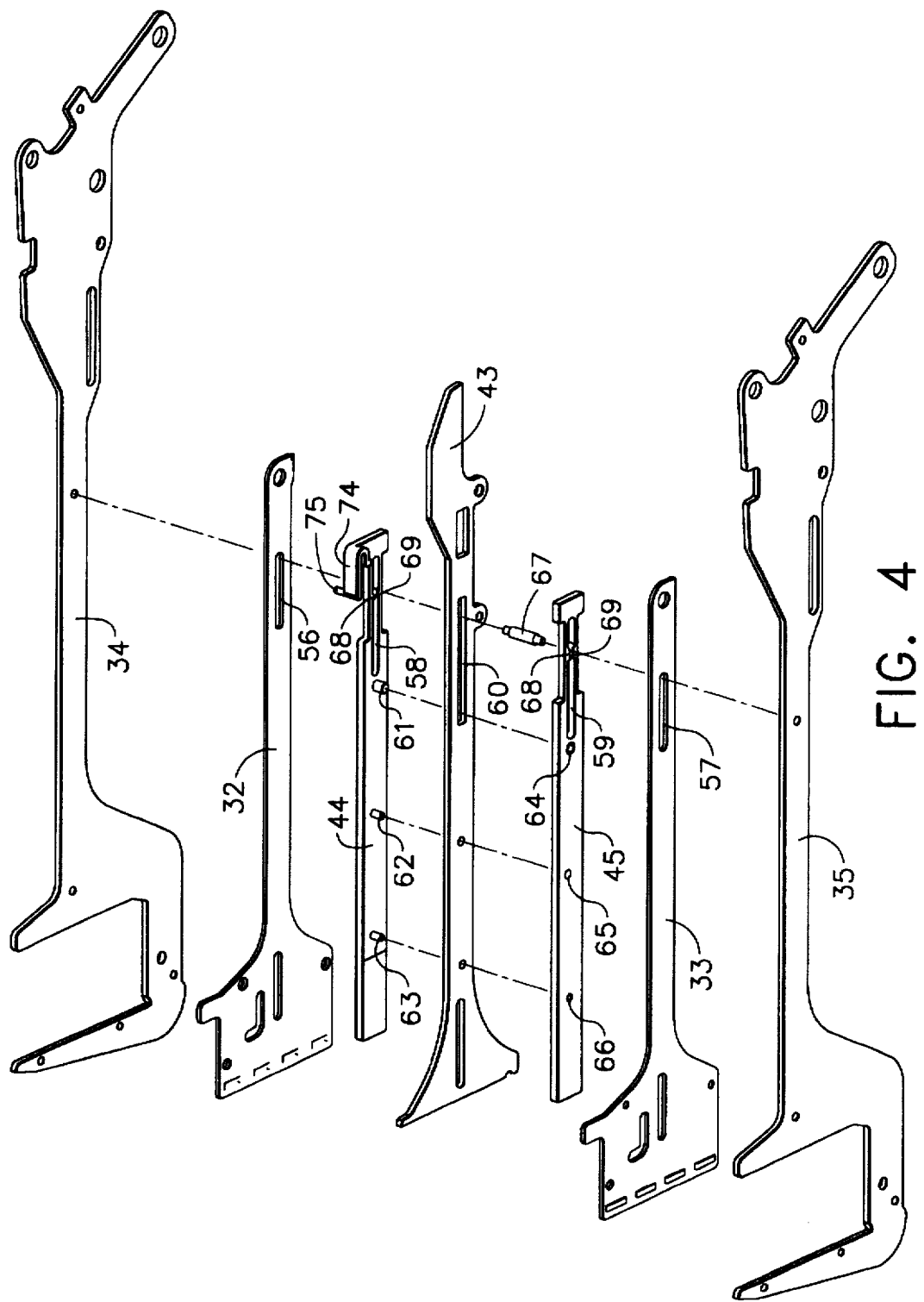
FIG. 4 is an exploded isometric view of the elongated plates and firing bar of the clamping and firing transmission assembly of the surgical linear stapler of FIG. 1.

Referring now to FIG. 4, the interrelationship between the hooks, closure plates, spacer plates and the firing bar will be described. The right and left hand closure plates have right and left hand elongated closure plate slots 56 and 57, respectively. Similarly, the right and left hand spacer plates have right and left hand spacer plate slots 58 and 59, respectively. Finally, the firing bar has an elongated firing bar slot 60. The location and length of the right hand slots for the right hand closure and spacer plates are substantially the same as the location and length of the corresponding left hand slots for the left hand closure and spacer plates. The length of the closure plate slots is shorter than the length of the spacer plate slots and firing bar slot. The length of the spacer plate slots is about the same as the length of the firing bar slot.

The spacer plates are fixed to the firing bar. Three posts, 61, 62 and 63, are mounted on the right hand spacer plate and extend through the firing bar into three corresponding receiving holes, 154, 65 and 66 on the left hand spacer plate.

A stationary slot pin 67 connects the right hand hook to the left hand hook. The stationary slot pin extends through the slots of the closure plates, spacer plates and the firing bar.

When the cartridge and anvil of the staple fastening assembly are in their spaced position, and the clamping trigger is in its open position, as best illustrated in FIG. 1, the distal ends of the slots in the components of the clamping and firing transmission assembly are substantially aligned with each other. Additionally, the stationary slot pin protrudes through the slots adjacent the distal end of each of the slots as shown in FIG. 5. When the clamping rigger is pivotally rotated from its open position toward the hand grip, the components of the clamping and transmission assembly move distally in tandem. When the clamping trigger has been pivotally rotated to its closed position, the stationary slot pin consequently is repositioned proximally of the distal end of the slots to an intermediate slot position which is best illustrated in FIG. 6. When the stationary slot pin is positioned in the intermediate slot position, the pin is positioned adjacent the proximal ends of the slots in the closure plates.

Figure 7:
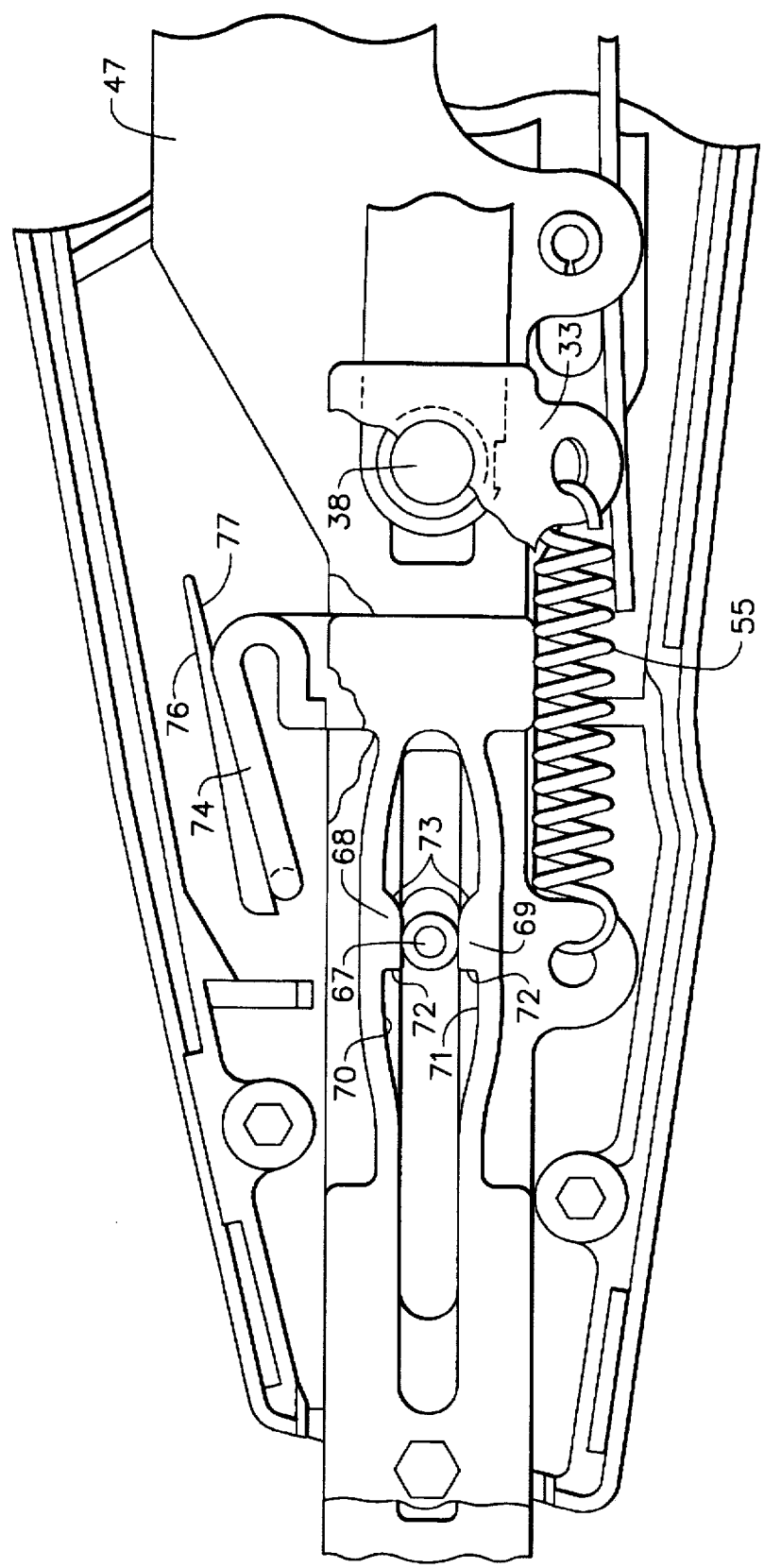
FIG. 7 is an enlarged fragmentary view of a portion of the truncated side elevation view of FIG. 5 when the firing trigger is pivotally rotated from its unfired position toward its fired position.
Figure 8:
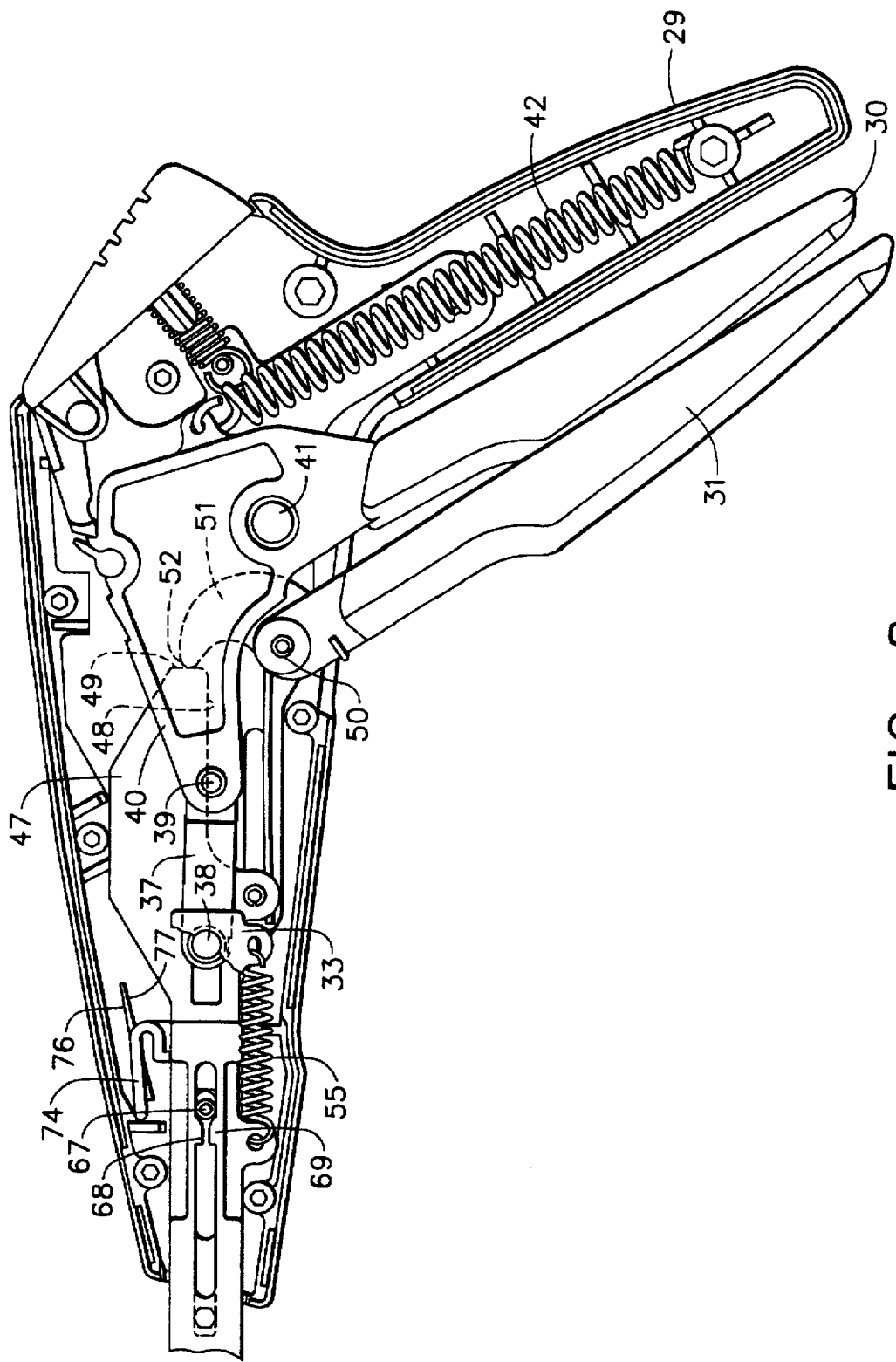
FIG. 8 is a truncated side elevation view as in FIG. 5 showing the firing trigger of the linear stapler in its fired position as shown in FIG. 3.

The mechanism for providing resistance against the pivotal rotation of the firing trigger independent of the staple fastening assembly will now be described in connection with FIG. 4 in combination more specifically with FIGS. 7 and 8. Adjacent to the intermediate slot position, each of the slots of the right and left hand spacer plates has first and second detents, 68 and 69, respectively. Upon closer study of FIG. 7, it can be observed that each slot has upper and lower ledges, 70 and 71, respectively. Each detent has a distal protruding surface 72 which is generally perpendicular to the slot ledge, and a proximal protruding surface 73 generally sloped from the ledge surface at an obtuse angle. When the firing trigger is in its unfired position, and the clamping trigger is in its closed position, as illustrated in FIG. 6, the stationary slot pin 67 rests close to or adjacent to the distal protruding surfaces of the first and second detents. When the firing trigger is subsequently pivotally rotated toward the clamping trigger, the spacer plates and firing bar move distally in tandem. Consequently, the first and second detents on the slots of the spacer plates are forced to cross over the stationary slot pin which is fixed to the hook plates. The detents cause the upper and lower ledges of the slots in the spacer plates to act as a pair of leaf springs to increase the resistance to pivotal rotation of the firing trigger. Without overcoming the resistance created by the detents, the firing trigger will not cause the firing bar to move distally to fire staples. As the resistance is being overcome, the detents provide the surgeon with the sense that staples are being formed. When the staples are formed, the detents have crossed over the stationary slot pin 67, and the stationary slot pin is positioned adjacent the proximal end of the slots of the spacer plates and the firing bar. Additionally, since the stationary pin is now positioned proximally of, and in close proximity to, proximal surface 73 of the first and second detents, the detents retain the firing trigger in its fired or fully actuated position. The positioning of the stationary slot pin 67 in the slots 58, 59 of the spacer plates and the firing bar 60 when the firing trigger is in its fully actuated position is illustrated in FIG. 8.

The mechanism for providing an audible signal to alert the surgeon when the staples have been fired is illustrated in FIG. 4 in combination more particularly with FIGS. 5–8. The right hand spacer plate has a signal spring 74 attached to the proximal end of the plate. The signal spring has a laterally extending signal pin 75. A signal ramp 76 is attached to the right hand shroud of the frame. When the clamping trigger is pivotally rotated from its open to closed positions, the signal spring is deflected downward as the signal pin slides along a sliding surface 77 of the signal ramp (see FIGS. 5 and 6). When the firing trigger is pivotally rotated toward the clamping trigger to fire staples, the signal pin of the signal spring continues to slide distally along the sliding surface of the signal ramp (see FIG. 7). When firing is completed, the signal pin slides off the distal end of the sliding surface of the signal ramp, and the distal end of the signal spring impacts the interior surface of the right hand shroud (see FIG. 8). This impact provides the surgeon with an audible signal that the staples have been fully formed.

Figure 9:
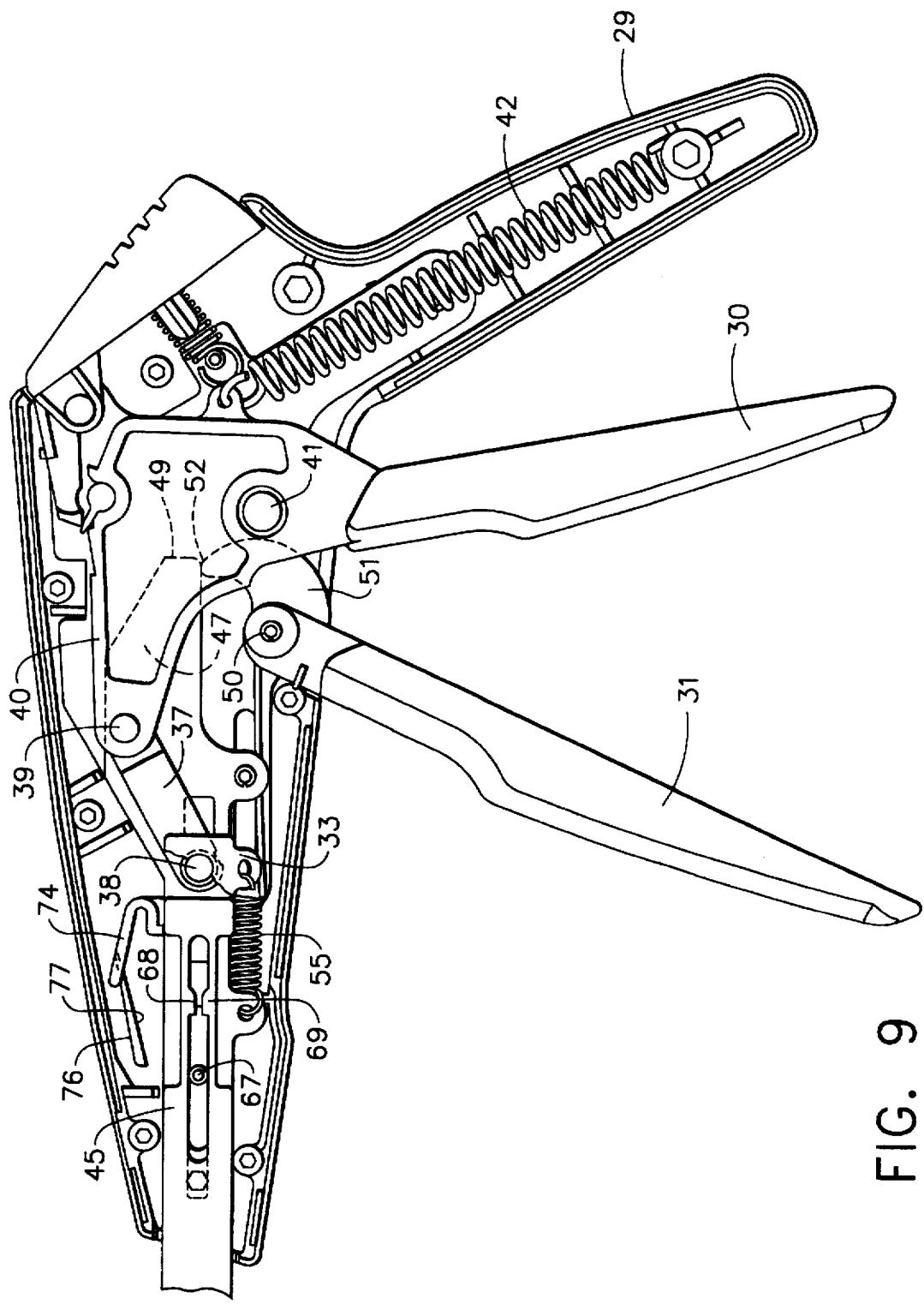
FIG. 9 is a truncated side elevation view as in FIG. 5 showing the clamping and firing triggers returning to their original positions.

The return of the clamping and firing triggers to their original, unactuated positions is illustrated in FIG. 9. Since the first and second detents have sloped proximal surfaces 73, the spacer plates create less resistance on the return stroke, thus lowering the load requirement for the firing bar return spring. The signal pin of the signal spring returns to its original position along the top of the signal ramp. The energy for this movement is supplied by the closure spring 42 and the firing bar return spring 55.

In another embodiment of this invention, if surface 73 of the first and second detents is positioned such that it is not in close proximity to the stationary pin after the firing trigger is fully actuated, then the firing trigger will return towards its original, unfired position.

Although this invention has been described in connection with its most preferred embodiments, numerous additional embodiments will become readily apparent to those skilled in this art. This description is intended to be illustrative only, and it is not intended to limit the scope or the spirit of the claimed invention as it is defined in the claims which appear below. For example, although the invention has been specifically described in connection with an open linear stapler, which is the most preferred embodiment, it is readily apparent that the invention is applicable to other surgical stapling instruments, including endoscopic linear staplers.

What is claimed is:

1. A surgical stapling instrument comprising:
   a) a frame at a first end of said instrument for gripping and manipulating said instrument, said frame having a body portion and a hand grip descending from said body portion thereof;
   b) a staple fastening assembly at an opposite end of said instrument, said staple fastening assembly including a cartridge displaying a plurality of vertical rows of slots for containing staples therein, and an anvil facing said cartridge for forming staples from said cartridge thereon, said cartridge and anvil movable towards each other from a spaced position for positioning tissue therebetween to a closed position for clamping the tissue;
   c) first and second elongated structural plates spaced from each other, said structural plates coupling said frame to said staple fastening assembly;
   d) a clamping and firing transmission assembly fitted between said structural plates, said clamping and firing transmission assembly including first and second elongated closure plates spaced from each other, said first closure plate adjacent said first structural plate and said second closure plate adjacent said second structural plate, and an elongated firing bar fitted between said closure plates;
   e) a clamping actuator at said frame and operatively connected to said clamping and firing transmission assembly, wherein when said clamping actuator is actuated, said clamping and firing transmission assembly moves distally causing said cartridge and anvil to move from their spaced position to their closed position for clamping the tissue;
   f) a firing trigger pivotally mounted to said body portion of said frame for pivotal counterclockwise rotation from an unfired position spaced from said hand grip to a fired position adjacent said hand grip, wherein when said firing trigger is stated from said unfired position to said fired position, said firing bar of said clamping and firing transmission assembly moves distally causing firing of said staples from said cartridge against said anvil for staple formation;
   g) first and second elongated spacer plates, said first spacer plate fitted between said first closure plate and said firing bar, and said second spacer plate fitted between said second closure plate and said firing bar, said spacer plates being secured to said firing bar; and
   h) means in communication with said clamping and firing transmission assembly independent of said staple fastening assembly for providing resistance to the distal movement of said firing bar when said firing trigger is pivotally rotated from said unfired position to said fired position; wherein:
   each of said closure and spacer plates, and said firing bar, has an elongated slot therein with proximal and distal ends;
   each closure plate slot has a first length, and each spacer plate slot and said firing bar slot has a second length, said second length being greater than said first length; and
   when said cartridge and anvil are in their spaced position, each of said slot distal ends is mutually aligned.

2. The instrument of claim 1 further comprising:

h) means in communication with said clamping and firing transmission assembly independent of said staple fastening assembly for providing a signal when said firing trigger is rotated to said fired position.

3. The instrument of claim 2 wherein said signal is an audible signal.

4. The instrument of claim 3 further comprising:

j) a stationary slot pin fixed to each of said structural plates through each of said slots;

wherein when said cartridge and anvil are in their spaced position, said stationary slot pin is initially located adjacent each of said slot distal ends;

when said clamping actuator is actuated to move said clamping and firing transmission assembly distally causing said cartridge and anvil to move to their closed position, each of said slots moves distally over said first length, and said stationary slot pin is intermediately located adjacent said slot proximal ends of each of said closure plates; and when said firing trigger is thereafter pivotally rotated to move each of said spacer plates and said firing bar distally so as to fire said staples, said slots of each of said spacer plates and said firing bar move distally from an intermediate slot position, and said stationary slot pin is finally located adjacent said slot proximal ends of each of said spacer plates and said firing bar.

5. The instrument of claim 4 wherein said resistance means includes first and second detents displayed on said elongated slots of each of said spacer plates, each of said detents is located adjacent said intermediate slot position, and when said firing trigger is pivotally rotated to fire said staples, each of said detents moves distally across said stationary slot pin.

6. The instrument of claim 5 wherein each of said spacer plate slots has upper and lower ledges, and each of said detents has a proximal and distal protruding surface extending from said upper and lower ledges, said distal protruding surface being generally perpendicular to said upper and lower ledges, and said proximal protruding surface being sloped in relation to said upper and lower ledges.

7. The instrument of claim 6 wherein said signal means includes:

a signal spring extending from one of said spacer plates, said signal spring having a signal pin thereon; and a signal ramp having a sliding surface thereon attached within said body portion of said frame;

wherein when said firing trigger is pivotally rotated from said unfired position, said signal spring is deflected as said signal pin slides on said sliding surface of said signal ramp; and when said firing trigger is pivotally rotated to said fired position, said signal pin slides off said sliding surface so as to deflect said pin against said body portion of said frame.

8. A surgical stapling instrument comprising:

a) a frame at a first end of said instrument for gripping and manipulating said instrument, said frame having a body portion and a hand grip descending from said body portion thereof;

b) a staple fastening assembly at an opposite end of said instrument, said staple fastening assembly including a cartridge displaying a plurality of vertical rows of slots for containing staples therein, an anvil facing said cartridge for forming said staples from said cartridge thereon, said cartridge and anvil movable towards each other from a spaced position for positioning tissue therebetween to a closed position for clamping the tissue;

c) a firing transmission assembly including an elongated firing bar interposed between said body portion of said frame and said staple fastening assembly;

d) a firing trigger pivotally mounted to said body portion of said frame for pivotal counterclockwise rotation from an unfired position spaced from said hand grip to a fired position adjacent said hand grip, wherein when said cartridge and anvil are in their closed position and said firing trigger is rotated from said unfired position to said fired position, said firing bar of said firing transmission assembly moves distally causing firing of staples from said cartridge against said anvil for staple formation;

e) a stationary slot pin fixed between said body portion of said frame and said staple fastening assembly, said stationary slot pin being received through an elongated slot in said firing transmission assembly; and f) a detent displayed on said elongated slot in said firing transmission assembly, and when said firing trigger is pivotally rotated to move said firing transmission assembly distally so as to fire said staples, said detent moves distally across said stationary slot pin so as to provide resistance to the distal movement of said firing bar.

9. The instrument of claim 8 further comprising:

f) means in communication with said firing transmission assembly independent of said staple fastening assembly for providing a signal when said firing trigger is rotated to said fired position.

10. The instrument of claim 9 wherein said signal is an audible signal.

11. The instrument of claim 10 wherein said detent has proximal and distal protruding surfaces extending from said elongated slot.

12. The instrument of claim 11 wherein said signal means includes:

a signal spring movable with said firing bar, said signal spring having a signal pin thereon; and a signal ramp having a sliding surface thereon attached within said body portion of said frame;

wherein when said firing trigger is pivotally rotated from said unfired position, said signal spring is deflected as said signal pin slides on said sliding surface of said signal ramp; and when said firing trigger is pivotally rotated to said fired position, said signal pin slides off said sliding surface so as to deflect said pin against said body portion of said frame.

* * * * *